US008609882B2

(12) United States Patent
Albalat et al.

(10) Patent No.: US 8,609,882 B2
(45) Date of Patent: Dec. 17, 2013

(54) PROCESS FOR DEACETALISATION OF α AMINOACETALS

(75) Inventors: Muriel Albalat, Coudoux (FR); Géraldine Primazot, Compiègne (FR); Didier Wilhelm, Issy les Moulineaux (FR); Jean-Claude Vallejos, La Ciotat (FR)

(73) Assignee: Clariant Speciality Fine Chemicals (France), Trosly Breuil (FR)

( * ) Notice: Subject to any disclaimer, the term of this patent is extended or adjusted under 35 U.S.C. 154(b) by 563 days.

(21) Appl. No.: 12/595,469

(22) PCT Filed: Apr. 2, 2008

(86) PCT No.: PCT/EP2008/053899
§ 371 (c)(1),
(2), (4) Date: Jan. 27, 2010

(87) PCT Pub. No.: WO2008/125486
PCT Pub. Date: Oct. 23, 2008

(65) Prior Publication Data
US 2010/0137633 A1    Jun. 3, 2010

(30) Foreign Application Priority Data
Apr. 11, 2007   (FR) ..................... 07 02633

(51) Int. Cl.
*C07C 269/04* (2006.01)
*C07C 227/00* (2006.01)
*C07C 229/02* (2006.01)
*C07C 271/18* (2006.01)

(52) U.S. Cl.
USPC ............. 560/29; 560/115; 560/129; 560/160; 560/164

(58) Field of Classification Search
None
See application file for complete search history.

(56) References Cited

U.S. PATENT DOCUMENTS

| 4,002,742 A * | 1/1977 | Wright et al. ................... 514/40 |
| 5,214,129 A * | 5/1993 | Luly et al. ..................... 530/331 |
| 5,329,025 A * | 7/1994 | Wong et al. ..................... 552/10 |
| 7,220,883 B2 | 5/2007 | Serradeil Albalat et al. |
| 2003/0149271 A1 | 8/2003 | Boesten et al. |
| 2005/0250795 A1* | 11/2005 | Leanna et al. ........... 514/263.38 |

FOREIGN PATENT DOCUMENTS

| EP | 0249349 | 12/1987 |
| EP | 0291234 | 11/1988 |
| EP | 0367242 | 5/1990 |
| EP | 0368719 | 5/1990 |
| EP | 0374647 | 6/1990 |
| EP | 0648758 | 4/1995 |
| EP | 1170289 | 1/2002 |
| FR | 2843112 | 2/2004 |
| WO | WO 96/14857 | 5/1996 |
| WO | WO 98/22496 | 5/1998 |
| WO | WO 0192199 | 12/2001 |
| WO | WO 2005087721 | 9/2005 |
| WO | WO 2007025307 | 3/2007 |

OTHER PUBLICATIONS

K.R. Muralidharan et al., Tetrahedron Lett., 1994, 35, 7489-7492.
Protective Groups in Organic Synthesis, 3rd edition, John Wiley & Sons, pp. 531-540, 1999.
May S.E. Denmark et al., Synlett., May 5, 1993, 359-361.
Heterocyclic Compounds, (1962), 3425-3428.
International Search Report for PCT/EP2008/053899, dated Jul. 21, 2008.
Translation of Written Opinion of the International Searching Authority for PCT/EP2008/053899, dated Jul. 21, 2008.
English Abstract for EP 0374647, Jun. 27, 1990.
Tetrahedron (1974), 30(23/24), 4233-4237.
Guillaumie, et al., "Solid—phase synthesis of C—terminal peptide aldehydes from amino acetals anchored to a backbone amide linker (BAL) handle", Tetrahedron Lett., 2000, 41(32), 6131-6135.
J. Med. Chem., 1987, 30(1), 150-156.
J. Org. Chem., 1981, 46(8), 1575-1585.
Bioorg. & Med. Chem. Lett., 2002, 12(4), 701-704.
J. Heterocycl. Chem., 1978, 15(4), 665-670.
D. Enders et al., Angew. Chem., Int. Ed. Engl., (1993), 32 (3), pp. 418-421.
J. Chem. Soc., 1957, 2146-2158.
Translation of Russian Patent Office Action for PCT/EP2008/053899, dated Mar. 29, 2012.

* cited by examiner

*Primary Examiner* — Rosalynd Keys
(74) *Attorney, Agent, or Firm* — Tod A. Waldrop

(57) ABSTRACT

The invention relates to a process for the preparation of N-protected α-aminoaldehydes by deacetalization of the acetal functional group of corresponding N-protected α-aminoacetals using formic acid.

10 Claims, No Drawings

PROCESS FOR DEACETALISATION OF α AMINOACETALS

The invention relates to a process for the preparation of N-protected α-aminoaldehydes by deacetalization of the acetal functional group of the corresponding N-protected α-aminoacetals.

In particular, the invention relates to a process for deacetalization of the acetal functional group of optically active α-aminoacetals without significant loss of enantiomeric excess in order to obtain the corresponding optically active α-aminoaldehydes, while retaining the optical stability.

α-Aminoacetals and in particular optically active α-aminoacetals are compounds which are highly advantageous as direct precursors, by deacetalization of the acetal functional group, of optically active α-aminoaldehydes.

Optically active α-aminoaldehydes are compounds commonly used as chiral reactants in total syntheses of biologically active products. However, this family of products is not readily available commercially.

This is because, on the one hand, α-aminoaldehydes are compounds having limited optical and chemical stabilities, which makes it difficult to synthesize them. Specifically, the stability of these products depends on the nature of the reaction medium and on the storage temperature but in particular on the nature of the protective group for the amine functional group. These compounds are accessible solely in the N-protected form in order to increase their stability during their synthesis and the reactions in which they are involved. The choice of the nature of the protective group is essential in this regard.

On the other hand, the most frequently described synthetic routes for the preparation of α-aminoaldehydes use α-amino acids as starting reactants (intermediate formation of a Weinreb amide, selective partial reduction of the carboxylic acid functional group or corresponding esters, or complete reduction to β-aminoalcohols and partial reoxidation). These methods of preparation exhibit various disadvantages, such as reaction conditions which limit industrial use, expensive reactants, and the like. The main constraint on these syntheses is the limited availability of the starting reactants, namely natural α-amino acids.

The use of N-protected α-aminoacetals, in the racemic form or in the optically active form, as precursors of N-protected α-aminoaldehydes would make it possible to overcome a large number of the problems mentioned above.

A stage of deacetalization of the acetal functional group on N-Boc-α-aminoacetals with 3 molar equivalents of trimethylsilyl iodide has been described in S. E. Denmark et al., Synlett., 1993, 5, 359-361. However, a loss of optical activity is observed for most of the products tested.

Likewise, K. R. Muralidharan et al., Tetrahedron Lett., 1994, 35, 7489-7492, deacetalized the acetal functional group of chiral N-benzyloxycarbonyl-α-aminoacetals in aqueous DMSO in order to access optically active N-benzyloxycarbonyl-α-aminoaldehydes. The deacetalization takes place without racemization but under restricting operating conditions (reflux in aqueous DMSO, purification on a flash column).

The operating conditions described in the prior art for accessing optically active α-aminoaldehydes by deacetalization of the acetal functional group of optically active α-aminoacetals are therefore not satisfactory for obtaining these products on an industrial scale.

The technical problem to be solved thus consists in providing a process for the preparation of N-protected α-aminoaldehydes, in the racemic form or in the optically active form, from the corresponding α-aminoacetals, while retaining the protection of the amine functional group and, if appropriate, while retaining optical activity in the case of optically active α-aminoacetals, which can be employed industrially.

It has now been found that, by combining the choice of a specific protective group for the amine functional group with an appropriate deacetalizing agent, it is possible to carry out the deacetalization of the acetal functional group under mild conditions and without significant loss of the enantiomeric excess, on the one hand, and without deprotecting the amine functional group, on the other hand, which makes it possible to obtain stable compounds.

Indeed, it has been found that the use of other protective groups for protecting the amine functional group, such as, for example, benzyl or tert-butoxycarbonyl (t-Boc) groups, does not make it possible to obtain this result.

The subject-matter of the invention is thus, according to a first aspect, a process for the preparation of N-protected α-aminoaldehydes, in the racemic or optically active form, comprising the stages consisting in:
protecting the amine functional group of the corresponding α-aminoacetals with an arylalkyloxycarbonyl group of general formula (I):

in which:
R represents a hydrogen, a phenyl group or a linear or branched $C_1$-$C_6$ alkyl group,
Ar represents a phenyl group, a naphthyl group or an anthryl group, optionally substituted by one or more halogen, phenyl, linear or branched $C_1$-$C_6$ alkyl, linear or branched $C_1$-$C_6$ alkoxy, nitro, cyano or methylsulphinyl groups, and
deacetalizing the acetal functional group of the said N-protected α-aminoacetals using formic acid.

Preferably, Ar represents a phenyl group and R represents a hydrogen.

The term "linear or branched $C_1$-$C_6$ alkyl" is understood to mean, for example, a methyl, ethyl, propyl, isopropyl, n-butyl, tert-butyl, isobutyl, pentyl or hexyl group.

The term "linear or branched $C_1$-$C_6$ alkoxy" is understood to mean, for example, a methoxy, ethoxy, propoxy, isopropoxy, n-butoxy, tert-butoxy, isobutoxy, pentoxy or hexoxy group.

The term "halogen" is understood to mean the fluorine, chlorine, bromine or iodine atoms.

Mention may be made, as examples of arylalkyloxycarbonyl group of general formula (I), of benzyloxycarbonyl, 4-phenylbenzyloxycarbonyl, 2-methylbenzyloxycarbonyl, 4-methoxybenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-methylsulphinylbenzyloxycarbonyl, 9-anthrylmethyloxycarbonyl or diphenylmethyloxycarbonyl.

According to a preferred aspect, the arylalkyloxycarbonyl group of general formula (I) is a benzyloxycarbonyl (Cbz) group.

According to a first alternative of the process according to the invention, use is made of N-protected α-aminoacetals, in the racemic form, of formula (II):

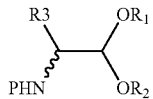

(II)

in which:
- $R_1$ and $R_2$, which are identical or different, represent a linear or branched $C_1$-$C_{12}$ alkyl group or else $R_1$ and $R_2$ are joined to form a 1,3-dioxolan-2-yl group which is unsubstituted or substituted on the 4 and/or 5 positions by one or more linear or branched $C_1$-$C_6$ alkyl substituents or a 1,3-dioxan-2-yl group which is unsubstituted or substituted on the 4 and/or 5 and/or 6 positions by one or more linear or branched $C_1$-$C_6$ alkyl substituents;
- $R_3$ represents a hydrogen; a linear or branched $C_1$-$C_{12}$ alkyl group; a $C_2$-$C_{12}$ alkenyl group; a $C_2$-$C_{12}$ alkynyl group; a $C_3$-$C_{10}$ cycloalkyl group; a $C_3$-$C_{10}$ cycloalkenyl group; a cycloalkylalkyl group in which the cycloalkyl and alkyl groups are as defined above; a heterocycloalkyl group including 3 to 10 atoms; a heterocycloalkylalkyl group in which the heterocycloalkyl and alkyl groups are as defined above; a monocyclic, bicyclic or tricyclic $C_6$-$C_{14}$ aryl group; a heteroaryl group including 5 to 14 atoms; an arylalkyl group or a heteroarylalkyl group in which the aryl, heteroaryl and alkyl groups are as defined above; a C(=O)$R_4$ group in which $R_4$ represents a linear or branched $C_1$-$C_{12}$ alkyl group, a cycloalkyl group, a cycloalkenyl group, a heterocycloalkyl group, an aryl group or a heteroaryl group as defined above, or $R_4$ represents an $OR_5$ group in which $R_5$ represents a hydrogen, a $C_1$-$C_{12}$ alkyl group, a $C_3$-$C_{10}$ cycloalkyl group, a $C_3$-$C_{10}$ cycloalkenyl group, a heterocycloalkyl group, an aryl group or a heteroaryl group as defined above, or $R_4$ represents an $NHR_6$ group in which $R_6$ represents a hydrogen, a linear or branched $C_1$-$C_{12}$ alkyl group, a $C_3$-$C_{10}$ cycloalkyl group, a $C_3$-$C_{10}$ cycloalkenyl group, a heterocycloalkyl group, an aryl group or a heteroaryl group as defined above; all the alkyl, alkenyl, alkynyl, cycloalkyl, cycloalkenyl, cycloalkylalkyl, heterocycloalkyl, heterocycloalkylalkyl, aryl, heteroaryl, arylalkyl or heteroarylalkyl radicals above being unsubstituted or substituted;
- P represents a group of formula (I) as defined above, and the acetal functional group is deacetalized using formic acid in order to obtain the N-protected α-aminoaldehydes, in the racemic form, of formula (III):

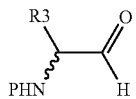

(III)

in which $R_3$ and P are as defined above.

Preferably, use will be made of the compounds of formula (II) in which:
- $R_1$ and $R_2$, which are identical or different, represent a linear or branched $C_1$-$C_6$ alkyl group, in particular methyl or ethyl;
- $R_3$ represents a group chosen from a linear or branched $C_1$-$C_6$ alkyl group which is substituted or unsubstituted; a monocyclic, bicyclic or tricyclic $C_6$-$C_{14}$ aryl group, preferably a phenyl group, which is substituted or unsubstituted; an arylalkyl group in which the aryl and alkyl groups are as defined above, preferably benzyl, which is substituted or unsubstituted; a $C_3$-$C_{10}$ cycloalkyl group, preferably a cyclohexyl group, which is substituted or unsubstituted; a cycloalkylalkyl group in which the cycloalkyl group and the alkyl group are as defined above, preferably a cyclobutylmethyl group;
- P represents Cbz.

Alternatively, the process according to the invention can be employed in order to obtain optically active N-protected α-aminoaldehydes of formulae (R)-(III) and (S)-(III) with a good reaction yield and a good optical purity from the corresponding optically active N-protected α-aminoacetals of formulae (R-(II) and (S)-(II).

According to this alternative, use is made of N-protected α-aminoacetals, in the optically active form, of formula (R-(II) or (S)-(II):

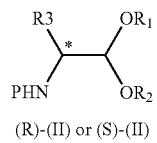

(R)-(II) or (S)-(II)

in which:
- the asterisk * means that the carbon atom is an asymmetric carbon,
- $R_1$, $R_2$ and P are as defined above for the formula (II),
- $R_3$ represents the same values as above, except for H, and the acetal functional group is deacetalized using formic acid in order to obtain the N-protected α-aminoaldehydes, in optically active form, of formula (R)-(III) or (S)-(III):

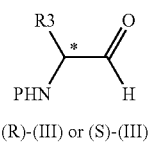

(R)-(III) or (S)-(III)

in which:
- the asterisk * means that the carbon atom is an asymmetric carbon,
- $R_3$ and P are as defined above.

Preferably, use will be made of the compounds of formula (R-(II) or (S)-(II) in which:
- $R_1$ and $R_2$, which are identical or different, represent a linear or branched $C_1$-$C_6$ alkyl group, in particular methyl or ethyl;
- $R_3$ represents a group chosen from a linear or branched $C_1$-$C_6$ alkyl group which is substituted or unsubstituted; a monocyclic, bicyclic or tricyclic $C_6$-$C_{14}$ aryl group, preferably a phenyl group, which is substituted or unsubstituted; an arylalkyl group in which the aryl and alkyl groups are as defined above, preferably benzyl, which is substituted or unsubstituted; a $C_3$-$C_{10}$ cycloalkyl group, preferably a cyclohexyl group, which is substituted or unsubstituted; a cycloalkylalkyl group in which the cycloalkyl group and the alkyl group are as defined above, preferably a cyclobutylmethyl group;

P represents Cbz.

According to another alternative, the process according to the invention can be employed in order to obtain optically active N-protected α-aminoaldehydes of formulae (R)-(V) and (S)-(V) with a good reaction yield and a good optical purity from the corresponding optionally active N-protected α-aminoacetals of formulae (R-(IV) and (S)-(IV), the optical stability of which is retained.

According to this alternative, use is made of N-protected α-aminoacetals, in optically active form, of formula (R-(IV) or (S)-(IV):

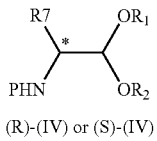

(R)-(IV) or (S)-(IV)

in which:
the asterisk * means that the carbon atom is an asymmetric carbon,
$R_1$, $R_2$ and P are as defined above for the formula (II),
$R_7$ represents a linear or branched $C_1$-$C_{12}$ alkyl group; a $C_2$-$C_{12}$ alkenyl group; a $C_2$-$C_{12}$ alkynyl group; a $C_3$-$C_{10}$ cycloalkyl group; a $C_3$-$C_{10}$ cycloalkenyl group; a cycloalkylalkyl group in which the cycloalkyl and alkyl groups are as defined above; a heterocycloalkyl group including 3 to 10 atoms; a heterocycloalkylalkyl group in which the heterocycloalkyl and alkyl groups are as defined above; an arylalkyl group in which the monocyclic, bicyclic or tricyclic aryl group is a $C_6$-$C_{14}$ aryl group and the alkyl group is as defined above; a heteroarylalkyl group in which the heteroaryl group includes 5 to 14 atoms and the alkyl group is as defined above; all the alkyl, alkenyl, alkynyl, cycloalkyl, cycloalkenyl, cycloalkylalkyl, heterocycloalkyl, heterocycloalkylalkyl, arylalkyl or heteroarylalkyl radicals above being unsubstituted or substituted,
and the acetal functional group is deacetalized using formic acid in order to obtain the N-protected α-aminoaldehydes, in the optically active form, of formula (R)-(V) or (S)-(V):

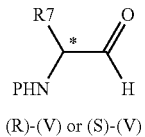

(R)-(V) or (S)-(V)

in which:
the asterisk * means that the carbon atom is an asymmetric carbon;
$R_7$ and P are as defined above.
Preferably, use will be made of compounds of formula (R)-(IV) or (S)-(IV) in which:
$R_1$ and $R_2$, which are identical or different, represent a linear or branched $C_1$-$C_6$ alkyl group, in particular a methyl or ethyl group;
$R_7$ represents a group chosen from a linear or branched $C_1$-$C_6$ alkyl group which is substituted or unsubstituted; an arylalkyl group in which the aryl and alkyl groups are as defined above, preferably a benzyl group, which is substituted or unsubstituted; a $C_3$-$C_{10}$ cycloalkyl group, preferably a cyclohexyl group, which is substituted or unsubstituted; a cycloalkylalkyl group in which the cycloalkyl group and the alkyl group are as defined above, preferably a cyclobutylmethyl group;
P represents Cbz.

In the present invention, the expression "optical stability retained" means without significant loss of enantiomeric excess, particularly up to approximately 5% loss, and more particularly without any loss of enantiomeric excess (within the measurement errors) on the carbon atom marked with an asterisk *.

Optional substituents of the $R_3$, $R_4$, $R_5$, $R_6$ and $R_7$ groups can be chosen independently from the halogen, OH, $NO_2$, $NH_2$, SH, $CO_2H$, CN, $SO_3H$, $CF_3$, alkoxycarbonyl (or alkyl-O—CO—), amide, alkyl-N—CO—, alkylenedioxy (or —O-alkylene-O—), alkylsulphinyl (or alkyl-SO—), alkylsulphonyl (or alkyl-$SO_2$—), alkylsulphonylcarbamoyl (or alkyl-$SO_2$—NH—C(=O)—), alkylthio (or alkyl-S—), —O-cycloalkyl, acyl (or r-CO—), acyloxy, acylamino, alkylamino, dialkylamino, arylamino, diarylamino, arylalkylamino, oxo (optionally protected in the form of a cyclic or noncyclic ketal), formyl (optionally protected in the form of a cyclic or noncyclic acetal), aryloxy, arylthio, heteroarylthio, alkyl, cycloalkyl, cycloalkenyl, aryl, arylalkyl, heteroaryl, alkenyl, alkynyl and alkoxy groups.

In the products of formula (II), (III), (IV) or (V), and also for the substituents, the groups indicated have the following meanings:
the halogen group denotes the fluorine, chlorine, bromine or iodine atoms;
the alkyl group denotes a linear or branched $C_1$-$C_{12}$ group, such as the methyl, ethyl, propyl, isopropyl, butyl, isobutyl, sec-butyl, tert-butyl, pentyl, isopentyl, sec-pentyl, tert-pentyl, neopentyl, hexyl, isohexyl, sec-hexyl, tert-hexyl, heptyl, octyl, nonyl, decyl, undecyl or dodecyl groups, linear or branched $C_1$-$C_6$ alkyl groups being preferred,
the alkenyl group denotes a linear or branched $C_2$-$C_{12}$ group, such as the ethenyl or vinyl, propenyl or allyl, 1-propenyl, n-butenyl, isobutenyl, 3-methylbut-2-enyl, n-pentenyl, hexenyl, heptenyl, octenyl or decenyl groups, linear or branched $C_2$-$C_4$ alkenyl groups being preferred;
the alkynyl group denotes a linear or branched $C_2$-$C_{12}$ group, such as the ethynyl, propynyl or propargyl, butynyl, n-butynyl, isobutynyl, 3-methylbut-2-ynyl, pentynyl or hexynyl groups, linear or branched $C_2$-$C_4$ alkynyl groups being preferred;
the alkoxy group denotes a linear or branched $C_1$-$C_{12}$ group, such as the methoxy, ethoxy, propoxy, isopropoxy, butoxy (linear, secondary or tertiary), pentoxy, hexoxy or heptoxy groups, linear or branched $C_1$-$C_6$ alkoxy groups being preferred;
the cycloalkyl group denotes a monocyclic or bicyclic $C_3$-$C_{10}$ carbocyclic group, such as the cyclopropyl, cyclobutyl, cyclopentyl or cyclohexyl groups;
the cycloalkenyl group denotes a monocyclic or bicyclic $C_3$-$C_{10}$ carbocyclic group comprising at least one double bond, such as the cyclobutenyl, cyclopentenyl or cyclohexenyl groups;
the cycloalkylalkyl group denotes a group in which the cycloalkyl and alkyl residues have the meanings indicated above, such as the cyclopropylmethyl, cyclobutylmethyl, cyclopentylmethyl, cyclohexylmethyl, cycloheptylmethyl, cyclopropylethyl or cyclohexylethyl groups;
the aryl group denotes an unsaturated, monocyclic, bicyclic or tricyclic, $C_6$-$C_{14}$ carbocyclic group, such as the phenyl, naphthyl, indenyl or anthracenyl groups and more particularly the phenyl group;

the arylalkyl group denotes a group in which the aryl and alkyl residues have the meanings mentioned above, such as the benzyl, phenylethyl, 2-phenylethyl or naphthylmethyl groups;

the heterocycloalkyl group denotes a monocyclic or bicyclic carbocyclic group including 3 to 10 atoms which is interrupted by one or more identical or different heteroatoms chosen from oxygen, nitrogen and sulphur atoms, such as the dioxolanyl, dioxanyl, dithiolanyl, thioxolanyl, oxiranyl, piperazinyl, piperidinyl, pyrrolidinyl, imidazolidinyl, pyrazolidinyl, morpholinyl, tetrahydrofuryl, tetrahydrothienyl or thiazolidinyl groups;

the heterocycloalkylalkyl group denotes a group in which the heterocycloalkyl and alkyl residues have the meanings mentioned above;

the heteroaryl group denotes an unsaturated or partially unsaturated, monocyclic, bicyclic or tricyclic, carbocyclic group with is interrupted by one or more identical or different heteroatoms chosen from the oxygen, nitrogen and sulphur atoms and which includes 5 to 14 atoms, such as the furyl (for example 2-furyl), thienyl (for example 2-thienyl or 3-thienyl), pyrrolyl, diazolyl, thiazolyl, isothiazolyl, oxazolyl, oxadiazolyl, 3- or 4-isoxazolyl, imidazolyl, pyrazolyl, isoxazolyl, pyridyl (for example 2- or 3- or 4-pyridyl), pyrimidyl, pyrimidinyl, pyridazinyl, pyrazinyl, tetrazolyl, benzothienyl (for example 3-benzothienyl), benzofuranyl, indolyl, purinyl, quinolyl, isoquinolyl, chromanyl or naphthyridinyl groups;

the heteroarylalkyl group denotes a group in which the heteroaryl and alkyl residues have the meanings mentioned above;

the alkyl-O—CO— group denotes a linear or branched $C_2$-$C_{12}$ group in which the alkyl group has the meaning indicated above;

the alkylene group denotes a linear or branched divalent $C_1$-$C_6$ hydrocarbon group, such as methylene, ethylene, propylene and isopropylene;

the —O-alkylene-O— group denotes a linear or branched $C_1$-$C_6$ group in which the alkylene group has the meaning indicated above;

the alkyl-SO— group denotes a linear or branched $C_1$-$C_{12}$ group in which the alkyl group has the meaning indicated above;

the alkyl-SO$_2$— group denotes a linear or branched $C_1$-$C_{12}$ group in which the alkyl group has the meaning indicated above;

the alkylsulphonylcarbamoyl group denotes a linear or branched $C_2$-$C_{12}$ group in which the alkyl group has the meaning indicated above;

the alkylthio group denotes a linear or branched $C_1$-$C_{12}$ group in which the alkyl group has the meaning indicated above, such as methylthio, ethylthio, isopropylthio and heptylthio;

the —O-cycloalkyl group denotes a group in which the cycloalkyl group has the meaning indicated above;

the r-CO— group denotes a linear or branched $C_2$-$C_{12}$ group in which r represents an alkyl, alkenyl, cycloalkyl, cycloalkenyl, heterocycloalkyl, aryl or heteroaryl group, these groups having the values indicated above, such as the acetyl, propionyl, butyryl, benzoyl, valeryl, hexanoyl, acryloyl and crotonoyl groups;

the acyloxy group denotes an acryl-O— group in which the acyl group has the meaning indicated above, such as acetoxy and propionyloxy;

the acylamino group denotes an acryl-N— group in which the acyl group has the meaning indicated above, such as acetamido;

the alkyl-N—CO— group denotes a group in which the alkyl group has the meaning indicated above;

the alkylamino, dialkylamino, arylamino, diarylamino or arylalkylamino groups denote groups in which the alkyl and aryl groups have the meanings indicated above;

the aryloxy group denotes an aryl-O— group in which the aryl group has the meaning indicated above, such as phenoxy or naphthyloxy;

the arylthio group denotes an aryl-S— group in which the aryl group has the meaning indicated above, such as phenylthio or naphthylthio;

the heteroarylthio group denotes a heteroaryl-S— group in which the heteroaryl group has the meaning indicated above, such as the thiophenethio group.

The stage of protection of the amine functional group with the P group and more particularly with the benzyloxycarbonyl (Cbz) group can be carried out by application or adaptation of the methods described in the literature, such as the work Protective Groups in Organic Synthesis, 3rd edition, John Wiley & Sons, pages 531-540. This reaction generally takes place in the presence of a chloroformate, such as benzyl chloroformate, in an amount of between 1 and 1.5 molar equivalents, preferably in an equimolar amount, and of a base, such as sodium hydroxide, triethylamine, sodium bicarbonate or potassium carbonate, in an amount of between 1 and 1.5 molar equivalents of base and preferably 1.2 molar equivalents of base, in an inert solvent or mixture of inert solvents, preferably in a two-phase medium, such as toluene/water or methyl tert-butyl ether (MTBE)/water, at a temperature of between −15° C. and ambient temperature, for a time of between 1 h and 24 h.

The stage of deacetalization with formic acid can be carried out under the following preferred conditions:

the formic acid is used in a proportion of 1 to 30 molar equivalents, preferably 20 and 25 molar equivalents, the deacetalization is optionally carried out in the presence of water in an amount of between 0.01 and 0.1 equivalent by weight with respect to the formic acid, preferably 0.05 equivalent by weight, the temperature is between 0 and 50° C., preferably between ambient temperature and 40° C., the pressure is between atmospheric pressure and 40 kPa, the time is between 1 h and 24 h.

The racemic α-aminoacetals used as starting material in the process of the invention can be prepared by adaptation of methods described in the literature, for example from α-halogenated acetals followed by amination, as described, by way of indication, in Heterocyclic Compounds, (1962), 3425, J. Chem. Soc., 1957, 2146-2158, J. Med. Chem., 1987, 30(1), 150-156 and J. Org. Chem., 1981, 46(8), 1575-1585. They can also be obtained from α-amino acids, followed by formation of a Weinreb amide, reduction and acetalization, as described in Bioorganic & Medicinal Chemistry Letters, 2002, 12(4), 701-704 and WO 9822496.

FR 2 843 112 describes the addition of organometallic compounds to aminotriazole derivatives, making it possible to obtain racemic or optically active α-aminoacetals.

The reduction of oxime derivatives of α-ketoacetals described in Journal of Heterocyclic Chemistry, 1978, 15(4), 665-670 and EP 3 672 42 also makes it possible to obtain racemic α-aminoacetals.

Optically active α-aminoacetals can also be obtained by adaptation of methods known in the literature, such as, for example, from α-amino acids, followed by formation of a Weinreb amide, reduction with a hydride and acetalization, as described in Tetrahedron Lett., 2000, 41(32), 6131-6135, WO 9822496 and WO 9614857, or reduction to give the alcohol, re-oxidation to give the aldehyde and acetalization, as described in Tetrahedron Lett., 2000, 41(32), 6131-6135, EP 291 234 and EP 249 349.

Use may also be made of the asymmetric reduction of optically active imines described in EP 374 647. Other routes by asymmetric induction are also described, such as the SAMP/RAMP method (Angew. Chem. Int. Ed. Engl., (1993), 32(3), 418-421) or also the use of chiral aminotriazoles (FR 2 843 112).

Generally, any known process for the preparation of an optically active α-aminoacetal is suitable for the invention, such as the Rosenmund reduction process described in particular in Tetrahedron (1974), 30(23/24), 4233-4237.

The compounds of formula (II), R-(II), S-(II), (III), R-(III) or S-(III) can be employed in the preparation of products having a pharmacological activity. These compounds are of particular use in the preparation of the SCH-503034 protease inhibitor described, for example, in WO 2005087721 and very particularly in the preparation of the intermediates 10.10 (tert-butyl ester of 2-carbamoyl-1-cyclobutylmethyl-2-hydroxyethylcarbamic acid) or 10.11 (3-amino-4-cyclobutyl-2-hydroxybutyramide hydrochloride).

The use of an N-protected α-aminoacetal of formula (II) in the racemic form or in the optically active form of formula (R)-(II) or (S)-(II) as defined above,

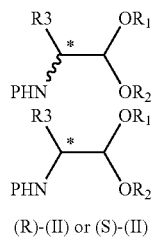

and the use of an N-protected α-aminoaldehyde of formula (III) in the racemic form or in the optically active form of formula (R)-(III) or (S)-(III) as defined above, with the exception of the cycloalkylalkyl group in the definition of $R_3$,

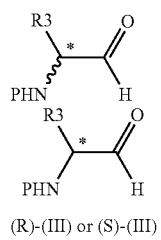

in the preparation of products having a pharmacological activity represent a subsequent aspect of the invention.

The invention thus also relates, according to another subsequent aspect, to the compounds of formula (II), (R)-(II) or (S)-(II) as defined above in which $R_1$ and $R_2$, which are identical or different, represent a linear or branched $C_1$-$C_{12}$ alkyl group, preferably a methyl group, P represents a benzyloxycarbonyl (Cbz) group and $R_3$ represents a cycloalkylalkyl group in which the cycloalkyl group is a $C_3$-$C_{10}$ cycloalkyl group and the linear or branched alkyl group is a $C_1$-$C_{12}$ alkyl group, preferably the cyclobutylmethyl group.

The following examples illustrate the invention in a non-limiting way.

The Nuclear Magnetic Resonance (NMR) analyses were carried out on a Brücker AC200 device in standard deuterated solvents (CDCl$_3$, d$_6$-DMSO, and the like). The gas chromatography (GC) analyses were carried out on a Varian 3900 device (FID detection) with a Chrompack column (30 m/CP-SIL 8 CB-low bleed MS/1 μm/0.25 mm) and, as method of analysis: T°$_{injector}$ 250° C./T°$_{detector}$ 300° C./oven programming: 80° C. for 1 min, then 15° C./min up to 300° C., and maintenance at 300° C.

EXAMPLE 1

Benzyl 1-isobutyl-2,2-dimethoxyethylcarbamate (Formula II: $R_1$=$R_2$=methyl; $R_3$=isobutyl; P=Cbz)

5 g of 1-isobutyl-2,2-dimethoxyethylamine (31 mmol, 1 mol. eq.) are dissolved in an MTBE (25 g)/H$_2$O (15 g) mixture in the presence of potassium carbonate (2.6 g, 18 mmol, 0.6 mol. eq.) in a 100 ml three-necked flask equipped with a reflux condenser, a dropping funnel, a magnetic stirrer and a thermometer. The medium is placed at a temperature of between 0° C. and 5° C. A solution of benzyl chloroformate (5.29 g, 31 mmol, 1 mol. eq.) in MTBE (10 g) is added dropwise to this reaction medium. At the end of the addition, the medium is maintained at a temperature of between 0° C. and 5° C. for 30 min and then slowly brought back to a temperature of 20-25° C. The medium is kept stirred at this temperature and the change in the reaction is monitored by GC analyses.

The reaction medium is separated by settling and the organic phase is concentrated. 8.85 g of benzyl 1-isobutyl-2,2-dimethoxyethylcarbamate are obtained (colourless oil, crude yield=97%).

Empirical formula: $C_{16}H_{25}NO_4$
Molar Mass: 295.38 g.mol$^{-1}$
GC analyses: t$_r$=18.1 min
NMR (200 MHz/CDCl$_3$):
$^1$H NMR: δ 0.84 (m, 6H, CH$_3$), 1.27 (m, 2H, CH$_2$), 1.59 (m, 1H, CH), 3.34 (s, 6H, CH$_3$), 3.8 (m, 1H, CH), 4.1 (distorted s, 1H, CH), 4.75 (d, 1H, NH), 5.03 (s, 2H, CH$_2$) and 7.1-7.3 (m, 5H, H$_{aromatic}$) ppm.
$^{13}$C NMR: δ 21.82 (CH$_3$), 23.6 (CH$_3$), 24.59 (CH), 38.5 (CH$_2$), 50.8 (CH), 56.01 (CH$_3$), 56.16 (CH$_3$), 66.73 (CH$_2$), 106.63 (CH), 128.05-128.54-128.79 (CH$_{aromatic}$), 136.72 (C$_{aromatic}$) and 156.37 (C=O) ppm.

EXAMPLE 2

Preparation of Compounds of Formula (II) in which:
$R_1$=$R_2$=methyl or ethyl
$R_3$=benzyl, isobutyl, phenyl, 4-methylbenzyl, 2-phenylethyl, cyclohexyl or —CH$_2$—CO$_2$Et
P=Cbz An α-aminoacetal corresponding to the N-protected α-aminoacetal of formula (II) (0.005 mol, 1 mol. eq.) is dissolved in a toluene or MTBE (4 g)/H$_2$O (3 g) mixture in the presence of potassium carbonate (0.003 mol, 0.6 mol. eq.) in a 50 ml three-necked flask equipped with a reflux condenser, a dropping funnel, a magnetic stirrer and a thermometer. The medium is placed in a temperature of between 0° C. and 5° C. A solution of benzyl chloroformate (0.005 mol, 1 mol. eq.) in toluene or MTBE (1 g) is added dropwise to this reaction medium. At the end of the addition, the medium is maintained at a temperature of between 0° C. and 5° C. for 30 min, then slowly brought back to a temperature of 20-25° C. and kept stirred at this temperature.

The reaction medium is separated by settling and the organic phase is concentrated. The expected product is obtained with a crude yield of 70% to quantitative.

Benzyl 1-benzyl-2,2-dimethoxyethylcarbamate (white solid)

Empirical formula: $C_{19}H_{23}NO_4$
Molar Mass: 329.40 g.mol$^{-1}$
GC analyses: $t_r$=25.1 min
NMR (200 MHz/CDCl$_3$):
$^1$H NMR: δ 2.8 (m, 2H, CH$_2$), 3.31 (s, 3H, CH$_3$), 3.35 (s, 3H, CH$_3$), 4.05 (m, 2H, CH), 4.95 (m, 3H, CH$_2$ and NH), 5.03 (s, 2H, CH$_2$) and 7.0-7.35 (m, 10H, H$_{aromatic}$) ppm.
$^{13}$C NMR: δ 36.13 (CH$_2$), 53.5 (CH), 55.69 (CH$_3$), 55.8 (CH$_3$), 66.67 (CH$_2$), 104.9 (CH), 126.45-129.39 (CH$_{aromatic}$), 136.7-137.9 (C$_{aromatic}$) and 156.13 (C=O) ppm.

Benzyl 1-phenyl-2,2-dimethoxyethylcarbamate (white solid)

Empirical formula: $C_{18}H_{21}NO$
Molar Mass: 315.37 g.mol$^{-1}$
GC analyses: $t_r$=22.8 min
NMR (200 MHz/CDCl$_3$):
$^1$H NMR: δ 3.25 (s, 3H, CH$_3$), 3.32 (s, 3H, CH$_3$), 4.3 (distorted d, 1H, CH), 4.8 (distorted d, 1H, CH), 5 (s, 2H, CH$_2$), 5.6 (distorted d, 1H, NH) and 7.0-7.25 (m, 10H, H$_{aromatic}$) ppm.
$^{13}$C NMR: δ 55.5 (CH$_3$), 57 (CH), 67 (CH$_2$), 106 (CH), 127-129 (CH$_{aromatic}$), 136-138 (C$_{aromatic}$) and 156 (C=O) ppm.
Melting point: M.p.=71° C.

Benzyl 1-(4-methylbenzyl)-2,2-dimethoxyethylcarbamate (white solid)

Empirical formula: $C_{20}H_{25}NO_4$
Molar Mass: 343.43 g.mol$^{-1}$
GC analyses: $t_r$=26.4 min
NMR (200 MHz/CDCl$_3$):
$^1$H NMR: δ 2.2 (s, 3H, CH$_3$), 2.77 (m, 2H, CH$_2$), 3.28 (s, 3H, CH$_3$), 3.32 (s, 3H, CH$_3$), 4 (m, 1H, CH), 4.08 (distorted d, 1H, CH), 4.58 (s, 1H, NH), 4.95 (s, 2H, CH$_2$) and 7.1-7.3 (m, 9H, H$_{aromatic}$) ppm.
$^{13}$C NMR (DEPT 135): δ 20.88 (CH$_3$), 35.5 (CH$_2$), 53.4 (CH), 55.4 (CH$_3$), 55.5 (CH$_3$), 66.4 (CH$_2$), 104.6 (CH) and 126.8-129.1 (CH$_{aromatic}$) ppm.
Melting point: M.p.=80° C.

Benzyl 1-(2-phenylethyl)-2,2-dimethoxyethylcarbamate (white solid)

Empirical formula: $C_{20}H_{25}NO_4$
Molar Mass: 343.43 g.mol$^{-1}$
GC analyses: $t_r$=27.4 min
NMR (200 MHz/CDCl$_3$):
$^1$H NMR: δ 1.7 (m, 1H, AB syst, CH$_2$), 1.9 (m, 1H, AB syst, CH$_2$), 2.7 (m, 2H, CH$_2$), 3.4 (s, 6H, CH$_3$), 3.85 (m, 1H, CH), 4.21 (d, 1H, J=3.2 Hz, CH), 5 (d, 1H, NH), 5.15 (s, 2H, CH$_2$) and 7.1-7.5 (m, 10H, H$_{aromatic}$) ppm.
$^{13}$C NMR: δ 31.55 (CH$_2$), 32.2 (CH$_2$), 52.5 (CH), 55.9 (CH$_3$), 56.07 (CH$_3$), 66.9 (CH$_2$), 106.2 (CH), 125.9-128.7 (CH$_{aromatic}$) 136.6 and 141.9 (C$_{aromatic}$) and 156.4 (C=O) ppm.
Melting point: M.p.=73° C.

Benzyl 1-cyclohexyl-2,2-dimethoxyethylcarbamate (colourless oil)

Empirical formula: $C_{18}H_{27}NO_4$
Molar Mass: 321.42 g.mol$^{-1}$
GC analyses: $t_r$=22.7 min
NMR (200 MHz/CDCl$_3$):
$^1$H NMR: δ 0.9-1.6 (m, 11H, CH+CH$_2$), 3.3 (s, 3H, CH$_3$), 3.32 (s, 3H, CH$_3$), 3.6 (m, 1H, CH), 4.21 (d, 1H, J=2.2 Hz, CH), 4.86 (d, 1H, NH), 5.0 (m, 2H, CH$_2$) and 7.1-7.4 (m, 5H, H$_{aromatic}$) ppm.
$^{13}$C NMR: δ 26.07-26.18-26.32-28.5-30.2 (CH$_2$), 39.0 (CH), 54.94 (CH$_3$), 55.15 (CH$_3$), 56.46 (CH), 66.65 (CH$_2$), 104.35 (CH), 127.95-128.43 (CH$_{aromatic}$), 136.75 (C$_{aromatic}$) and 156.76 (C=O) ppm.

Ethyl 3-(benzyloxycarbonylamino)-4,4-diethoxybutyrate

Empirical formula: $C_{18}H_{27}NO_6$
Molar Mass: 353.42 g.mol$^{-1}$
GC analyses: $t_r$=20.7 min
NMR (200 MHz/CDCl$_3$):
$^1$H NMR: δ 1-1.3 (m, 9H, CH$_3$), 2.6 (m, 2H, CH$_2$), 3.6 (m, 4H, CH$_2$), 4.15 (m, 3H, CH+CH$_2$), 4.5 (d, 1H, CH), 5.1 (s, 2H, CH$_2$), 5.35 (d, 1H, NH) and 7.2-7.5 (m, 5H, CH$_{aromatic}$) ppm.
$^{13}$C NMR (DEPT 135): δ 13.95 (CH$_3$), 14.99 (CH$_3$), 15.03 (CH$_3$), 34.4 (CH$_2$), 50.1 (CH), 60.4 (CH$_2$), 63.4 (CH$_2$), 63.85 (CH$_2$), 66.55 (CH$_2$), 102.2 (CH) and 128.29-127.9 (CH$_{aromatic}$) ppm.

Ethyl 3-(benzyloxycarbonylamino)-4,4-dimethoxybutyrate

Empirical formula: $C_{16}H_{23}NO_6$
Molar Mass: 325.36 g.mol$^{-1}$
GC analyses: $t_r$=20.06 min
NMR (200 MHz/CDCl$_3$):
$^1$H NMR: δ 1.2 (t, 3H, CH$_3$), 2.55 (m, 2H, CH$_2$), 3.4 (s, 6H, CH$_3$), 4.15 (m, 3H, CH+CH$_2$), 4.35 (m, 1H, CH), 5.1 (s, 2H, CH$_2$), 5.3 (d, 1H, NH) and 7.2-7.5 (m, 5H, CH$_{aromatic}$) ppm.
$^{13}$C NMR (DEPT 135): δ 13.1 (CH$_3$), 33.5 (CH$_2$), 48.6 (CH), 54.3 (CH$_3$), 54.9 (CH$_3$), 59.6 (CH$_2$), 65.8 (CH$_2$), 103.8 (CH) and 127.06-127.47 (CH$_{aromatic}$) ppm.

EXAMPLE 3

Benzyl 1-benzyl-2-oxoethylcarbamate (Formula (III): R$_3$=benzyl, P=Cbz)

9.3 g of N-Cbz-1-benzyl-2,2-dimethoxyethylamine (0.028 mol, 1 mol. eq.), 32.5 g of 98% formic acid (0.70 mol, 25 mol. eq.) and 1.7 g of water are introduced into a 100 ml round-bottomed flask equipped with a magnetic stirrer and a reflux condenser. The medium is kept stirred at a temperature of 20-25° C. for 8 h.

25 g of H$_2$O and 60 g of MTBE are added to the reaction medium. Separation by settling is carried out and the organic phase is washed with 4.25 g of H$_2$O and then with a 10% aqueous K$_2$CO$_3$ solution in order to remove any remaining trace of formic acid (4.25 ml). The organic phase is dried over MgSO$_4$ and concentrated. 7.8 g of benzyl ester of 1-benzyl-2-oxoethylcarbamic acid are obtained (quantitative crude yield).

Empirical formula: C$_{17}$H$_{17}$NO$_3$
Molar Mass: 283.33 g.mol$^{-1}$
GC analyses: t$_r$=23.5 min
NMR (200 MHz/CDCl$_3$):
$^1$H NMR: δ 3.05 (d, 2H, CH$_2$), 4.3 (m, 1H, CH), 5.05 (s, 2H, CH$_2$), 5.4 (s, 1H, NH), 7.1-7.6 (m, 10H, H$_{aromatic}$) and 9.5 (s, 1H, CHO) ppm.
$^{13}$C NMR (DEPT 135): δ 35.8 (CH$_2$), 61.5 (CH), 67.5 (CH$_2$), 127.6-129.7 (CH$_{aromatic}$) and 199.3 (CHO) ppm.

EXAMPLE 4

Benzyl 1-isobutyl-2-oxoethylcarbamate (Formula (III): R$_3$=isobutyl, P=Cbz)

10.9 g of N-Cbz-1-isobutyl-2,2-dimethoxyethylamine (0.037 mol, 1 mol. eq.), 34.1 g of 98% formic acid (0.74 mol, 20 mol. eq.) and 2.3 g of water are introduced into a 100 ml round-bottomed flask equipped with a magnetic stirrer and a reflux condenser. The medium is kept stirred at a temperature of 20-25° C. for 4 h.

25 g of H$_2$O and 60 g of MTBE are added to the reaction medium. Separation by settling is carried out and the organic phase is washed with 4.20 g of H$_2$O and then with a 10% aqueous K$_2$CO$_3$ solution in order to remove any remaining trace of formic acid (4.25 ml), and then the organic phase is dried over MgSO$_4$ and concentrated. 9.2 g of benzyl ester of 1-isobutyl-2-oxoethylcarbamic acid are obtained (quantitative crude yield).

Empirical formula: C$_{14}$H$_{19}$NO$_3$
Molar Mass: 249.31 g.mol$^{-1}$
GC analyses: t$_r$=17.4 min
NMR (200 MHz/CDCl$_3$):
$^1$H NMR: δ 0.9 (m, 6H, CH$_3$), 1.45-1.8 (m, 3H, CH$_2$+CH), 4.4 (m, 1H, CH), 5.15 (s, 2H, CH$_2$), 5.25 (s, 1H, NH$_2$), 7.2-7.5 (s, 5H, H$_{aromatic}$) and 9.6 (s, 1H, CHO) ppm.
$^{13}$C NMR: δ 21.97 (CH$_3$), 23.1 (CH$_3$), 24.7 (CH), 38.2 (CH$_2$), 58.9 (CH), 67.2 (CH$_2$), 128.2-128.8 (CH$_{aromatic}$) and 136.2 (C$_{aromatic}$), 156.3 (0=0) and 199.7 (CHO) PPM.

EXAMPLE 5

Benzyl 1-cyclobutylmethyl-2,2-dimethoxyethylcarbamate (Formula (II): R$_1$=R$_2$=methyl, R$_3$=cyclobutylmethyl, P=Cbz)

1-Cyclobutylmethyl-2,2-dimethoxyethylamine (13.05 g, 0.075 mol, 1 mol. eq.) is dissolved in an MTBE (35 g)/H$_2$O (25 g) mixture in the presence of potassium carbonate (6.22 g, 0.045 mol, 0.6 mol. eq.) in a 250 ml three-necked flask equipped with a reflux condenser, a dropping funnel, a magnetic stirrer and a thermometer. The medium is placed in a cold bath. A solution of benzyl chloroformate (12.79 g, 0.075 mol, 1 mol. eq.) in MTBE (10 g) is added dropwise to this reaction medium. At the end of the addition, the medium is maintained in the cold bath and the return at ambient temperature takes place slowly with stirring.

After separating the reaction medium by settling, the aqueous phase is extracted with MTBE and the organic phase is washed with H$_2$O and then dried over MgSO$_4$. After concentrating the organic phase, 21.05 g of the expected product are obtained with a crude yield of 91%.

Empirical formula: C$_{17}$H$_{25}$NO$_4$
Molar Mass: 307.39 g.mol$^{-1}$
NMR (200 MHz/CDCl$_3$):
$^1$H NMR: δ 1.4-2.2 (m, 8H, CH$_2$), 2.34 (m, 1H, CH), 3.4 (s, 3H, CH$_3$), 3.41 (s, 3H, CH$_3$), 3.75 (m, 1H, CH), 4.15 (distorted d, 1H, CH), 4.8 (distorted d, 1H, NH), 5.1 (s, 2H, CH$_2$) and 7.25-7.4 (m, 5H, H$_{aromatic}$) ppm.
$^{13}$C NMR: δ 18.55 (CH$_2$), 28.47 (CH$_2$), 28.6 (CH$_2$), 32.95 (CH), 36.56 (CH$_2$), 51.2 (CH), 55.77 (CH$_3$), 55.94 (CH), 66.6 (CH$_2$), 106.1 (CH), 127.97-128.42-128.52 (CH$_{aromatic}$), 136.6 (C$_{aromatic}$) and 156.1 (C=O) ppm.

EXAMPLE 6

Benzyl 1-cyclobutylmethyl-2-oxoethylcarbamate (Formula (III): R$_3$=cyclobutylmethyl, P=Cbz)

N-Cbz-1-cyclobutylmethyl-2,2-dimethoxyethylamine (11 g, 0.035 mol, 1 mol. eq.) is introduced into a 95% aqueous formic acid solution (41.17 g, 0.89 mol, 25 mol. eq.; 2.16 g of H$_2$O) in a 250 ml round-bottomed flask equipped with a magnetic stirrer, a dropping funnel, a thermometer and a reflux condenser. The medium is kept stirred at ambient temperature for 2 h 40.

40 g of H$_2$O and 80 g of MTBE are added to the reaction medium. Separation by settling is carried out and the organic phase is washed several times with a K$_2$CO$_3$ solution (73 g in 150 g of H$_2$O) and with H$_2$O. The organic phase is dried over MgSO$_4$ and concentrated. 8.2 g of the expected product are obtained, i.e. a crude yield of 90%.

Empirical formula: C$_{15}$H$_{19}$NO$_3$
Molar Mass: 261.32 g.mol$^{-1}$
NMR (200 MHz/CDCl$_3$):
$^1$H NMR: δ 1.4-2.1 (m, 8H, CH$_2$), 2.3 (m, 1H, CH), 4.15 (m, 1H, CH), 5.05 (s, 2H, CH$_2$), 5.25 (d, 1H, NH), 7.2-7.4 (m, 5H, H$_{aromatic}$) and 9.47 (s, 1H, CHO) ppm.
$^{13}$C NMR: δ 18.4 (CH$_2$), 28.58 (CH$_2$), 28.65 (CH$_2$), 32.27 (CH), 36.2 (CH$_2$), 59.4 (CH), 67 (CH$_2$), 128.05-128.7 (CH$_{aromatic}$), 136.12 (C$_{aromatic}$), 155.91 (C=O) and 199.2 (CHO) ppm.

EXAMPLE 7

Analysis of the Optical Stability after Deacetalization

In order to carry out this analysis, an optically active α-aminoacetal of formula (R-(IV) in which R$_1$=R$_2$=ethyl, R$_7$=—CH$_2$—CO$_2$Et and P=Cbz is deacetalized, corresponding to an N-protected α-aminoaldehyde, and then this is reacetalated, according to the following scheme.

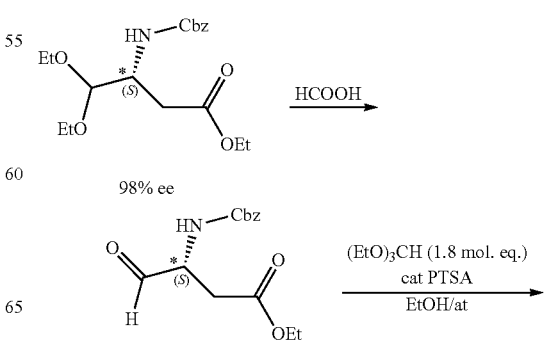

-continued

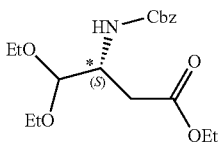

98% ee

The enantiomeric purity is measured with regard to the optically active N-protected α-aminoacetal obtained after reacetalization. The enantiomeric purity is measured by the enantiomeric excess, which corresponds to the ratio of the excess of the desired enantiomer with respect to the undesired enantiomer.

This ratio is calculated according to one of the following equations:

% ee.(R)=([R]−[S]/[R]+[S])×100

% ee.(S)=([S]−[R]/[R]+[S])×100 in which:
% ee.(R) represents the enantiomeric excess of R isomer
% ee.(S) represents the enantiomeric excess of S isomer
[R] represents the concentration of R isomer and
[S] represents the concentration of S isomer.

Ethyl (S)-3-(benzyloxycarbonylamino)-4,4-diethoxybutyrate (enantiomeric purity=98% ee, determined by chiral HPLC) (1 mol. eq.) is introduced into a 95% aqueous formic acid solution (25 mol. eq.) in a 50 ml round-bottomed flask equipped with a magnetic stirrer and a reflux condenser. The medium is kept stirred at ambient temperature for 2 to 5 h.

$H_2O$ and MTBE are added to the reaction medium. Separation by settling is carried out and the organic phase is washed several times with $H_2O$ and then with a 10% aqueous $K_2CO_3$ solution in order to remove any remaining trace of formic acid, and then dried over $MgSO_4$ and concentrated. The residue is stored in a refrigerator overnight and then stirred at ambient temperature in absolute EtOH in the presence of approximately 1.8 mol. eq. of $CH(OEt)_3$ and 0.1 mol. eq. of para-toluenesulphonic acid (PTSA) for 24 h.

$H_2O$ is added and the mixture is concentrated in EtOH, then the PTSA is neutralized with $K_2CO_3$ and extraction is carried out with MTBE. The organic phase is concentrated. The residue is analysed by chiral HPLC: an enantiomeric purity of 98% ee is obtained, which shows the absence of measurable racemization during the stage of deacetalization of the acetal functional group.

Chiral HPLC analyses: Chiralcel OD-H, hexane/isopropanol (95/5), 1 ml/min, UV detection 254 nm and polarimeter.

EXAMPLE 8

In order to study the optical stability of the optically active α-aminoaldehydes of formula (S)-(V) or (R)-(V) in which $R_1$, $R_2$ and $R_7$ are defined in Table 1 below, which are obtained during the reaction for the deacetalization of the acetal functional group with formic acid, on the one hand the N-protected α-aminoaldehydes of formula (R)-(V) or (S)-(V) are reacetalated to give the corresponding α-aminoacetals of formula (R-(IVb) or (S)-(IVb) and, on the other hand, the N-protected α-aminoaldehydes of formula (R)-(V) or (S)-(V) are converted to the corresponding α-aminoalcohols of formula (R)-(VI) or (S)-(VI), as shown in Scheme 1 below:

Scheme 1

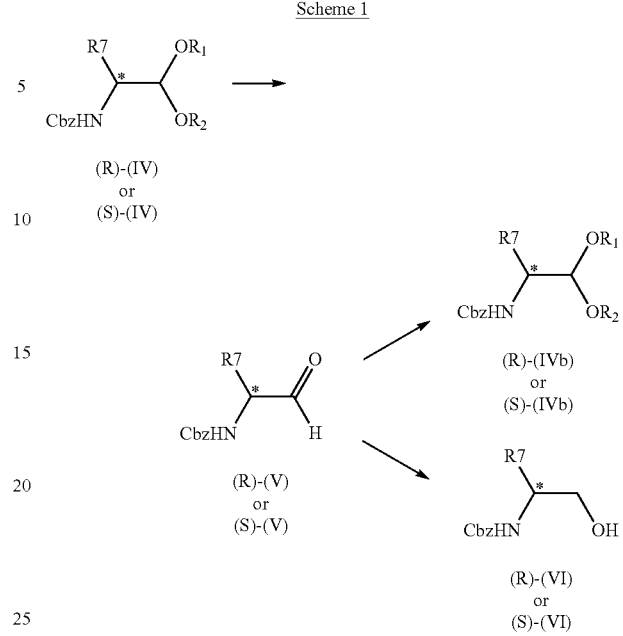

The results obtained are reported in Table 1 below.

TABLE 1

| $R_1$ | $R_2$ | $R_7$ | $ee_{[V]}$ % | $ee_{[IVb]}$ % | $ee_{[VI]}$ % |
|---|---|---|---|---|---|
| Methyl | Methyl | Isobutyl | 92(S) | 92(S) | 92(S) |
| Methyl | Methyl | Benzyl | 70(R) | 71(R) | |
| Ethyl | Ethyl | $CH_2COOEt$ | 98(S) | 98(S) | |

$ee_{[V]}$: Enantiomeric purity, determined by chiral HPLC
$ee_{[IVb]}$: Enantiomeric purity, determined by chiral HPLC after a stage of reacetalization of (V) to give (IVb).
$ee_{[VI]}$: Enantiomeric purity, determined by chiral HPLC after a stage of reduction of (V) to give aminoalcohol (VI).

Chiral HPLC Analyses:
Chiralcel OD-H, hexane/isopropanol (90/10 or 95/5), 1 ml/min, UV detection 254 nm and polarimeter,
Chiralpak AD, hexane/isopropanol (90/10), 1 ml/min, UV detection 254 nm and polarimeter.

The results show the optical stability of the optically active α-aminoaldehydes of formula (R-(V) or (R)-(V) obtained during the reaction for the deacetalization of the acetal functional group.

EXAMPLE 9

Comparative Example

A test of deacetalization of the acetal functional group using benzyl as protective group for the amine functional group was carried out.

1 g of N,N-dibenzyl-1-methyl-2,2-dimethoxyethylamine (3.3 mmol, 1 mol. eq.) and 17.6 g of formic acid in 2.4 g of $H_2O$ are introduced into a 50 ml three-necked flask equipped with a thermometer, a reflux condenser and a magnetic stirrer. The medium is left stirring at ambient temperature for 5 days (no change recorded by GC). The medium is heated at 40° C. for 9 h.

The starting material remains intact.

This result shows that it is not possible to deacetalize the acetal functional group with formic acid using the benzyl protective group.

EXAMPLE 10

Comparative Example

A test of deacetalization of the acetal functional group using the tert-butyloxycarbonyl (tBoc) group as protective group for the amine functional group was carried out.

1 g of tert-butyl 1-methyl-2,2-dimethoxyethylcarbamate (4.5 mmol, 1 mol. eq.) and 1.7 ml of formic acid are introduced into a 50 ml three-necked flask equipped with a thermometer, a reflux condenser and a magnetic stirrer. The medium is left stirring at ambient temperature for 30 h.

The starting material remains intact.

This result shows that it is not possible to deacetalize the acetal functional group with formic acid using the tBoc protective group.

EXAMPLE 11

Comparative Example

A test of deacetalization of the acetal functional group using the Cbz group as protective group for the amine functional group and acetic acid as deacetalizing agent was carried out.

0.25 g of benzyl 1-benzyl-2,2-dimethoxyethylcarbamate (0.76 mmol, 1 mol. eq.) and 1.25 g of 95% aqueous acetic acid are introduced into a 50 ml two-necked flask equipped with a thermometer, a reflux condenser and a magnetic stirrer. The medium is left stirring at ambient temperature for 24 h.

The starting material remains intact (monitored by GC).

The medium is subsequently left stirring at a temperature of between 40 and 80° C. for 8 h. The starting material still remains intact.

After 5 h at reflux, the starting material decomposes.

This result shows that it is not possible to deacetalize the acetal functional group with the Cbz protective group for the amine functional group using acetic acid as deacetalizing agent.

The invention claimed is:

1. A process for the preparation of a N-protected α-aminoaldehyde, in the racemic or optically active form, comprising the steps of:
   protecting the amine functional group of the corresponding α-aminoacetal with an arylalkyloxycarbonyl group of general formula (I):

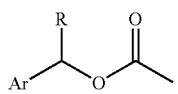

(I)

wherein:
R is a hydrogen, a phenyl group or a linear or branched $C_1$-$C_6$ alkyl group,
Ar is a phenyl group, a naphthyl group or an anthryl group, optionally substituted by one or more halogen, phenyl, linear or branched $C_1$-$C_6$ alkyl, linear or branched $C_1$-$C_6$ alkoxy, nitro, cyano or methylsulphinyl groups, and
deacetalizing the acetal functional group of the said N-protected α-aminoacetal using formic acid.

2. A process according to claim 1, wherein the arylalkyloxycarbonyl group is chosen from benzyloxycarbonyl, 4-phenylbenzyloxycarbonyl, 2-methyl-benzyloxycarbonyl, 4-methoxybenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxy-carbonyl, 3-bromobenzyloxycarbonyl, 4-nitrobenzyloxycarbonyl, 4-cyanobenzyl-oxycarbonyl, 4-methylsulphinylbenzyloxycarbonyl, 9-anthrylmethyloxycarbonyl and diphenylmethyloxycarbonyl.

3. A process according to claim 1, wherein the N-protected α-aminoacetal is in the racemic form, of formula (II):

wherein:
$R_1$ and $R_2$, are identical or different and are a linear or branched $C_1$-$C_{12}$ alkyl group,
or else $R_1$ and $R_2$ are joined to form a 1,3-dioxolan-2-yl group unsubstituted or substituted on the 4 and/or 5 position(s) by one or more linear or branched $C_1$-$C_6$ alkyl substituents or a 1,3-dioxan-2-yl group unsubstituted or substituted on the 4 and/or 5 and/or 6 position(s) by one or more linear or branched $C_1$-$C_6$ alkyl substituents;
$R_3$ is a hydrogen; a linear or branched $C_1$-$C_{12}$ alkyl group; a $C_2$-$C_{12}$ alkenyl group; a $C_2$-$C_{12}$ alkynyl group; a $C_3$-$C_{10}$ cycloalkyl group; a $C_3$-$C_{10}$ cycloalkenyl group; a cycloalkylalkyl group wherein the cycloalkyl and alkyl groups are as defined above; a heterocycloalkyl group including 3 to 10 atoms; a heterocycloalkylalkyl group wherein the heterocycloalkyl and alkyl groups are as defined above; a monocyclic, bicyclic or tricyclic $C_6$-$C_{14}$ aryl group; a heteroaryl group including 5 to 14 atoms; an arylalkyl group or a heteroarylalkyl group wherein the aryl, heteroaryl and alkyl groups are as defined above; a C(=O)$R_4$ group wherein $R_4$ is a linear or branched $C_1$-$C_{12}$ alkyl group, a $C_3$-$C_{10}$ cycloalkyl group, a $C_3$-$C_{10}$ cycloalkenyl group, a heterocycloalkyl group including 3 to 10 atoms, an aryl group or a heteroaryl group as defined above, or $R_4$ is an $OR_5$ group wherein $R_5$ is a hydrogen, a linear or branched $C_1$-$C_{12}$ alkyl group, a $C_3$-$C_{10}$ cycloalkyl group, a $C_3$-$C_{10}$ cycloalkenyl group, a heterocycloalkyl group, an aryl group or a heteroaryl group as defined above, or $R_4$ is an $NHR_6$ group wherein-$R_6$ is a hydrogen, a linear or branched $C_1$-$C_{12}$ alkyl group, a $C_3$-$C_{10}$ cycloalkyl group, a $C_3$-$C_{10}$ cycloalkenyl group, a heterocycloalkyl group, an aryl group or a heteroaryl group as defined above; all the alkyl, alkenyl, alkynyl, cycloalkyl, cycloalkenyl, cycloalkylalkyl, heterocycloalkyl, heterocycloalkylalkyl, aryl, heteroaryl, arylalkyl or heteroarylalkyl radicals above being unsubstituted or substituted; and
P is a group of formula (I),

(I)

comprising the step of deacetalizing the acetal functional group using formic acid in order to obtain the N-protected α-aminoaldehyde, in the racemic form, of formula (III):

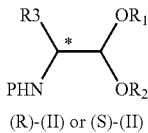

(III)

wherein R₃ and P are defined above.

4. A process according to claim 1, wherein the N-protected α-aminoacetal, is in the optically active form, of formula (R)-(II) or (S)-(II):

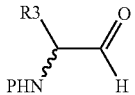

(R)-(II) or (S)-(II)

wherein:

the asterisk * means that the carbon atom is an asymmetric carbon, $R_1$ and $R_2$, are identical or different, and are a linear or branched $C_1$-$C_{12}$ alkyl group, or else $R_1$ and $R_2$ are joined to form a 1,3-dioxolan-2-yl group unsubstituted or substituted on the 4 and/or 5 position(s) by one or more linear or branched $C_1$-$C_6$ alkyl substituents or a 1,3-dioxan-2-yl group unsubstituted or substituted on the 4 and/or 5 and/or 6 position(s) by one or more linear or branched $C_1$-$C_6$ alkyl substituents;

$R_3$ is a linear or branched $C_1$-$C_{12}$ alkyl group; a $C_2$-$C_{12}$ alkenyl group; a $C_2$-$C_{12}$ alkynyl group; a $C_3$-$C_{10}$ cycloalkyl group; a $C_3$-$C_{10}$ cycloalkenyl group; a cycloalkylalkyl group wherein the cycloalkyl and alkyl groups are defined above; a heterocycloalkyl group including 3 to 10 atoms; a heterocycloalkylalkyl group wherein the heterocycloalkyl and alkyl groups are defined above; a monocyclic, bicyclic or tricyclic $C_6$-$C_{14}$ aryl group; a heteroaryl group including 5 to 14 atoms; an arylalkyl group or a heteroarylalkyl group wherein the aryl, heteroaryl and alkyl groups are defined above; a C(=O)R₄ group in which R₄ is a linear or branched $C_1$-$C_{12}$ alkyl group, a $C_3$-$C_{10}$ cycloalkyl group, a $C_3$-$C_{10}$ cycloalkenyl group, a heterocycloalkyl group, an aryl group or a heteroaryl group as defined above, or R₄ is an OR₅ group wherein R₅ is a hydrogen, a linear or branched $C_1$-$C_{12}$ alkyl group, a $C_3$-$C_{10}$ cycloalkyl group, a $C_3$-$C_{10}$ cycloalkenyl group, a heterocycloalkyl group, an aryl group or a heteroaryl group as defined above, or R₄ is an NHR₆ group wherein R₆ is a hydrogen, a linear or branched $C_1$-$C_{12}$ alkyl group, a $C_3$-$C_{10}$ cycloalkyl group, a $C_3$-$C_{10}$ cycloalkenyl group, a heterocycloalkyl group, an aryl group or a heteroaryl group as defined above; all the alkyl, alkenyl, alkynyl, cycloalkyl, cycloalkenyl, cycloalkylalkyl, heterocycloalkyl, heterocycloalkylalkyl, aryl, heteroaryl, arylalkyl or heteroarylalkyl radicals above being unsubstituted or substituted; and P is a group of formula (I),

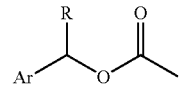

(I)

comprising the step of deacetalizing the acetal functional group using formic acid in order to obtain the N-protected α-aminoaldehyde, in optically active form, of formula (R)-(III) or (S)-(III):

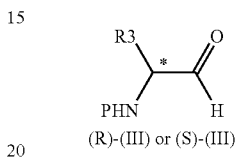

(R)-(III) or (S)-(III)

wherein:

the asterisk * means that the carbon atom is an asymmetric carbon, and R₃ and P are defined above.

5. A process according to claim 1, wherein the N-protected α-aminoacetal, is in the optically active form, of formula (R)-(IV) or (S)-(IV):

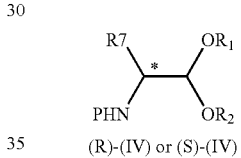

(R)-(IV) or (S)-(IV)

wherein:

the asterisk * means that the carbon atom is an asymmetric carbon, $R_1$ and $R_2$, are identical or different, and are a linear or branched $C_1$-$C_{12}$ alkyl group or else $R_1$ and $R_2$ are joined to form a 1,3-dioxolan-2-yl group unsubstituted or substituted on the 4 and/or 5 position(s) by one or more linear or branched $C_1$-$C_6$ alkyl substituents or a 1,3-dioxan-2-yl group unsubstituted or substituted on the 4 and/or 5 and/or 6 position(s) by one or more linear or branched $C_1$-$C_6$ alkyl substituents;

$R_7$ is a linear or branched $C_1$-$C_{12}$ alkyl group; a $C_2$-$C_{12}$ alkenyl group, a $C_2$-$C_{12}$ alkynyl group; a $C_3$-$C_{10}$ cycloalkyl group; a $C_3$-$C_{10}$ cycloalkenyl group; a cycloalkylalkyl group wherein the cycloalkyl and alkyl groups are defined above; a heterocycloalkyl group including 3 to 10 atoms; a heterocycloalkylalkyl group wherein the heterocycloalkyl and alkyl groups are defined above; an arylalkyl group in which the monocyclic, bicyclic or tricyclic aryl group is a $C_6$-$C_{14}$ aryl group and the alkyl group is as defined above; a heteroarylalkyl group wherein the heteroaryl group includes 5 to 14 atoms and the alkyl group is defined above; all the alkyl, alkenyl, alkynyl, cycloalkyl, cycloalkenyl, cycloalkylalkyl, heterocycloalkyl, heterocycloalkylalkyl, arylalkyl or heteroarylalkyl radicals above being unsubstituted or substituted; and P is a group of formula (I),

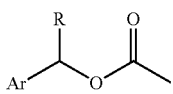

comprising the step of deacetalizing the acetal functional group using formic acid in order to obtain the N-protected α-aminoaldehyde, in the optically active form, of formula (R)-(V) or (S)-(V):

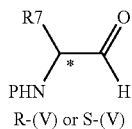

R-(V) or S-(V)

wherein:

the asterisk * means that the carbon atom is an asymmetric carbon;

$R_7$ and P are defined above.

6. A process according to claim 1, wherein in the deacetalizing step, the formic acid is used in a proportion of 1 to 30 molar equivalents.

7. A process according to claim 1, wherein the deacetalizing step is carried out in the presence of water in an amount of between 0.01 and 0.1 equivalent by weight with respect to the formic acid.

8. A compound of formula (II), (R)-(II) or (S)-(II):

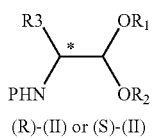

(R)-(II) or (S)-(II)

wherein:

$R_1$ and $R_2$, are identical or different, and are a linear or branched $C_1$-$C_{12}$ alkyl group;

$R_3$ is a cycloalkylalkyl group wherein the cycloalkyl group is a $C_3$-$C_{10}$ cycloalkyl group and the linear or branched alkyl group is a $C_1$-$C_{12}$ alkyl group;

P is a benzyloxycarbonyl group, and the asterisk * means that the carbon atom is an asymmetric carbon.

9. A process according to claim 1, wherein in the deacetalizing step, the formic acid is used in a proportion of 20 to 25 molar equivalents.

10. A process according to claim 1, wherein in the deacetalizing step is carried out in the presence of water in an amount of 0.05 equivalent by weight, with respect to the formic acid.

* * * * *